United States Patent [19]
Brady et al.

[11] Patent Number: 5,558,747
[45] Date of Patent: Sep. 24, 1996

[54] PROCESS FOR AZEOTROPIC DISTILLATION OF AQUEOUS CHLORAL MIXTURES

[75] Inventors: Kevin Brady, Hacienda Heights; Lester Friedmann, Long Beach, both of Calif.

[73] Assignee: AMVAC Chemical Corporation, Los Angeles, Calif.

[21] Appl. No.: 552,434

[22] Filed: Nov. 3, 1995

(Under 37 CFR 1.47)

Related U.S. Application Data

[63] Continuation of Ser. No. 83,831, Jun. 25, 1993, abandoned.
[51] Int. Cl.[6] ............................... B01D 3/36; C07C 45/84
[52] U.S. Cl. .............................. 203/17; 203/67; 203/73; 203/80; 568/492
[58] Field of Search ............................ 203/14, 17, 67, 203/73, 80; 568/492; 570/262

[56] References Cited

U.S. PATENT DOCUMENTS

| | | |
|---|---|---|
| 2,473,003 | 6/1949 | Beachell et al. . |
| 2,559,247 | 7/1951 | Goebel et al. . |
| 2,584,036 | 1/1952 | Mahoney et al. . |
| 2,746,912 | 5/1956 | Park et al. . |
| 2,759,978 | 8/1956 | Stevens et al. . |
| 4,263,269 | 4/1981 | Little et al. ............................... 203/49 |
| 4,311,563 | 1/1982 | Opavsky et al. ........................... 203/46 |
| 4,507,514 | 3/1985 | Ariki et al. ............................... 203/51 |
| 4,513,152 | 4/1985 | Schillawski . |
| 4,628,122 | 12/1986 | Kuntz et al. . |
| 4,814,528 | 3/1989 | Schussler et al. . |

FOREIGN PATENT DOCUMENTS

| | | |
|---|---|---|
| 102372 | 10/1979 | Poland . |
| 634398 | 3/1950 | United Kingdom . |

OTHER PUBLICATIONS

CA 91 (16): 129614 m Liquid—Vapor equilibriums for several Binary systems.

*Primary Examiner*—Virginia Manoharan
*Attorney, Agent, or Firm*—Loeb & Loeb LLP

[57] ABSTRACT

An improved process for azeotropic distillation of chloral to anhydrous chloral containing as little as 0.1% water. An azeotropic mixture is used which contains chloral in at least a 1.4:1 ratio with the concentration (% of weight) of a azeotropic agent (preferably ethylene dichloride). The feed stream may contain other components, but will contain at least 60% chloral and less than 40% water. Preferably, the feed stream is substantially free of components other than choral and water. Water is removed from the overhead product of the azeotropic and EDC separation distillations periodically or continuously throughout the process. The azeotropic agent is preferably separated from the anhydrous chloral product. This separation may be performed in the azeotropic distillation column or in a separate distillation column.

10 Claims, 2 Drawing Sheets

PROCESS FOR AZEOTROPIC DISTILLATION OF AQUEOUS CHLORAL MIXTURES

This is a continuation of application Ser. No. 08/083,831, filed on Jun. 25, 1993, now abandoned.

BACKGROUND OF THE INVENTION

1. Field of the Invention

This invention relates to the recovery of anhydrous chloral from a mixture containing chloral and water and/or chloral hydrate and other components. More particularly, it relates to a process for extracting 99.9% or more of the water from the chloral/water mixture by azeotropic distillation at atmospheric pressure using ethylene dichloride as an azeotroping agent and one or more distillation columns.

2. Description of Related Art

Over the years, there have been several methods employed to remove trichloroacetaldehyde (hereafter, "chloral") from aqueous solutions in which it is present. Where the separated chloral is to be used, for example, in other chemicals, it may be of critical importance that the chloral be as free of water as possible. In this context, the presence of even relatively minute quantities of water can have a substantially adverse effect on the performance of the end chloral product.

One of the more common approaches to the dehydration of chloral has been the use of azeotropic distillation. This processes involves contacting the chloral-containing solution with a dehydrating agent under conditions sufficient to form an azeotropic mixture. Examples of dehydrating agents which have been used in this process include benzene or n-hexane (see, e.g., U.S. Pat. No. 2,584,036), or hydrochloric acid (see, e.g., U.S. Pat. No. 2,746,912). Other process for the removal of water from chloral are known, for example, distillation from sulfuric acid (see, e.g., U.S. Pat. No. 4,513,152 and the patent references cited therein). However, all these processes produce chloral which is contaminated with solvent and/or contains a quantity of water which is unacceptable for many uses or have large waste streams associated with their practice.

Currently, as shown in U.S. Pat. Nos. 4,814,528 and 4,628,122, the aqueous by-product from the manufacture of vinyl chloride, ethylene dichloride, or in general, the oxychlorination of ethylene, must be incinerated or neutralized and destroyed prior to discharge or disposal.

One attempt to obtain dry chloral using ethylene dichloride or 1,2-dichloroethane (hereafter, "EDC") in an azeotropic distillation process is described by Schussler, et al, in U.S. Pat. No. 4,814,528. In the process described, EDC, the contained impurity, chloral and water are subjected to azeotropic distillation wherein EDC is used as the azeotropic agent resulting in a dried EDC containing chloral. At atmospheric pressure this process was described as only reducing the water content to between 1% and 3% by weight (relative to chloral content).

The percentage of water in the end product of the Schussler, et al. process was greatly decreased by application of superatmospheric pressure to the azeotropic mixture during distillation. Although more effective than prior art azeotropic distillations of chloral at atmospheric pressure, the Schussler, et al., approach requires use of specialized distillation equipment. As a result, this process suffers from increased manufacturing cost as well as operating risks associated with the use of pressurized liquids and gases. Further, this method would require processing extremely large volumes of EDC for relatively small amounts of isolated chloral. For example, the EDC to chloral ratio used for the work described in Schussler, et al., is between 94:1 and 171:1.

Using the same dehydrating agent (EDC), researchers at the Institute for Organic Industry in Warsaw and the Polytechnical University of Szozecin in Poland reported that they obtained 98.5–98.9% anhydrous chloral in an azeotropic distillation (see, Polish Patent No. 102,372 to Cieslak, et al., and Cieslak, et al., *Przem. Chem* 56 (11) 594–598 (1977)).

The focus of this process was the separation of dichloroacetaldehyde (DCA) from chloral, rather than the separation of chloral from water. The azeotropic mixture, therefore, included EDC, chloral, water and DCA. Further, because of the focus of the process on DCA recovery, it was directed toward separation of components from an acetaldehyde chlorination mixture of 80% or more chloral and up to 12.5% water. No teaching is provided regarding application of the process to other feed streams or of the process parameters, i.e., the amount of EDC and temperature ranges necessary to achieve the reported results.

What is needed, therefore is a method for producing very dry chloral which meets at least the following criteria:
1. An azeotropic mixture should be used which readily allows separation of water from the chloral without use of extreme operating conditions, i.e., elevated pressures or temperatures. Also, the chloral must be easily separable from the azeotropic agent and other components in the mixture without compromising the dehydration process. To this end, the azeotropic mixture will preferably be binary, i.e., it will be formed principally of the dehydrating agent and water.
2. Further, with respect to the first criteria, the dehydrating agent used in the process should be susceptible to separation from the anhydrous chloral product without significant contamination thereof.
3. The process should be tolerant of feed stream composition changes. In particular, the process should be effective in producing very dry chloral even from feed streams containing as much as 40% water by weight.
4. The process should also be effective with the use of a relatively broad range of chloral to dehydrating agent ratios (weight to weight).
5. The process should also provide a method for production of chloral having a water content of 0.1% by weight or less.
6. The process should also provide a relatively simple, cost-effective means of converting the aqueous waste streams from the manufacture of vinyl chloride, ethylene dichloride or, in general, the oxychlorination of ethylene, into a commercially viable product; e.g., technical chloral which can also be convened into other chloral-containing chemicals.

The present invention meets these above criteria, providing an improved process for preparation of anhydrous chloral.

SUMMARY OF THE INVENTION

The invention consists of a method for azeotropic distillation of chloral to anhydrous chloral. More specifically, according to the method of the invention, EDC is either contained in or is added to, an aqueous stream containing at least 60% chloral and up to 40% water. The process is operated entirely at normal atmospheric pressures or at those just above normal to the extent required by equipment or environmental concerns.

An exemplary distillation apparatus for use in practicing the inventive method is also disclosed. An apparatus which will be effectively used with the method will be one which includes at least one distillation column having at least 6 theoretical trays. Preferably, each distillation column will have at least 12 theoretical trays and most preferably will have 25–26 theoretical trays. The apparatus will be adapted to allow for removal of water from the overhead products of both the azeotropic and EDC separation distillations as they proceed to completion.

An apparatus which uses a single column for separation of the dehydrating agent from the chloral by distillation is preferred. In this embodiment, the single column will be elongated to include a greater number of theoretical trays as necessary. The process may be performed in a batchwise or continuous manner in both single and multiple column apparatuses.

Use of the method of this invention, in conjunction with other prior art, avoids production of waste streams from the manufacture of vinyl chloride, ethylene dichloride or the oxychlorination of ethylene by providing a relatively simple, cost-effective means of converting this waste product into a commercially viable one; e.g., very dry technical chloral which can also be converted into other chloral-containing chemicals.

For purposes of this application, the phrase "very dry chloral" refers to chloral product which is substantially free (to no more than trace amounts) of dehydrating agent and contains 0.1% water or less.

BRIEF DESCRIPTION OF THE DRAWINGS

Like reference numbers and designations in the various drawings refer to like elements.

DETAILED DESCRIPTION OF THE INVENTION

The feed stream from which chloral is to be extracted and dehydrated may be any composition which contains at least 60% chloral and less than 40% water. A particularly preferred source of the chloral is an aqueous stream resulting from the manufacture of ethylene dichloride or vinyl chloride. In the most preferred embodiment, the feed stream will be concentrated from an aqueous stream isolated from the oxychlorination of ethylene. The feed stream may, and often does, contain minor amounts of organic materials in addition to chloral.

Figure 1:
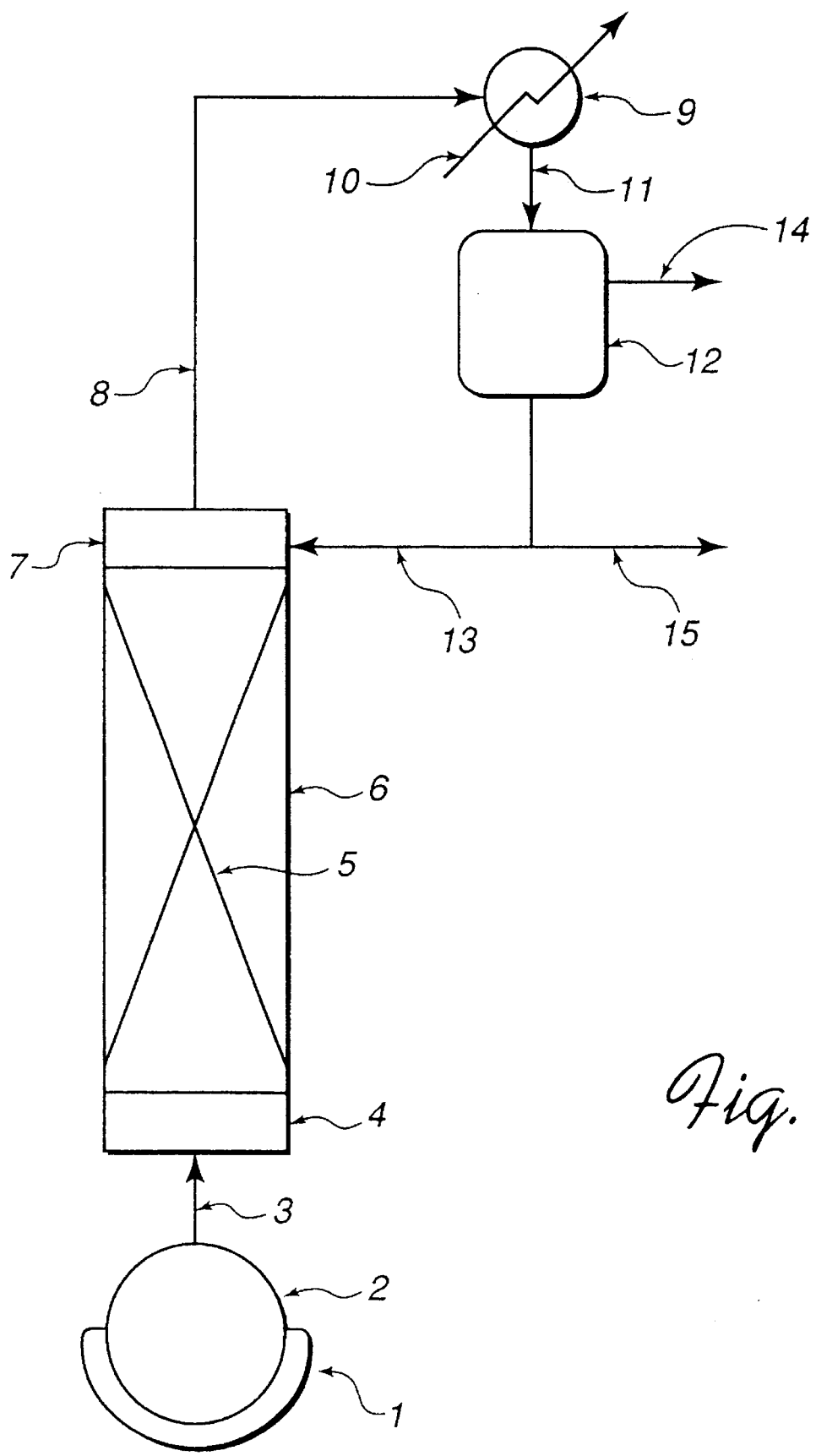
FIG. 1 schematically depicts an exemplary distillation apparatus for use in practicing the method of the invention. Flow of the charged stream through the apparatus and recovery of components therefrom are indicated by arrows at appropriate junctures in the Figure.

Referring to FIG. 1, a schematic of a distillation apparatus suitable for use with the method of the invention is shown. The direction of flow through the apparatus is indicated by arrows. For simplicity, certain mechanical components of the system such as pumps and valves are not described or shown but should be assumed to be present as appropriate in the apparatuses of FIGS. 1 and 2. Also, for simplicity instrument devices such as temperature sensing or flow controls are not described or shown but should be assumed to be present as appropriate in the apparatuses of FIGS. 1 and 2.

Although this particular configuration is shown, for the reasons discussed below, it will be appreciated by those skilled in the art that other configurations and components could be used in the distillation apparatus without substantially compromising the efficiency of the inventive method as long as means are provided for the removal of water from the overhead product. For example, the distillation column may be a multiple sectioned column, a bubble cap column, sieve plate column, or similar device. Sources of heat other than electrical, steam or hot heat transfer fluid may be used. Single condensers may be replaced with a plurality of condensers operating in series and/or parallel. Condensers or other vessels may be vented to permit removal of uncondensed gases. Columns of different lengths and diameters may also be used, although the column described infra is a preferred embodiment.

Referring now in detail to FIG. 1, there is shown a distillation pot 2, electrically heated with heating mantle 1. Still pot 2 is in turn in vapor communication with distillation column 6 at its bottom end 4. Distillation column 6 is 0.75 inches of internal diameter and 48.5 inches in total length containing packing material 5. Suitable packing materials are known to those skilled in the art; a preferred material is Raschig rings. Based on calibration methods known to those skilled in the art, the total number of theoretical plates in this column is 26.

In distillation column 6 and especially within the channels provided by packing material 5 the aqueous chloral composition is countercurrently contacted with reboiled and condensed vapors and liquid EDC. Overhead or head product from the distillation of the feed stream is passed from the top of the column 7 through line 8 into condenser 9 cooled by coolant passing through line 10. In condenser 9 most of the by-product composition is condensed to a liquid comprising an organic phase and an aqueous phase. The material is passed to decanter 12 through line 11. (Unless otherwise noted, all lines identified in this disclosure are sealably connected to each container they pass between). After separation of water from the EDC according to the described method, the EDC can be returned via line 13 for reflux through column 6 or alternatively can be drained from the system, either batchwise or continuously, through line 15. The separated liquid aqueous phase is removed, either batchwise or continuously, from decanter 12 via line 14.

On completion of the distillation process, still pot 2 will contain a mixture of chloral and EDC which is substantially free of water. According to one embodiment of the invention, the chloral is purified to be substantially free of EDC in a second distillation column which has essentially the same structure as the previously described apparatus. Processes for separation of chloral from EDC by distillation are well known in the art and will not therefore, be discussed in detail here.

Generally, therefore, the chloral/EDC mixture is transferred from still pot 2 to a second distillation apparatus for separation of the EDC from the chloral. The bottom product of this distillation will be chloral, which is tapped off from the still pot. The overhead product of this distillation will principally be EDC. This overhead product can then be recycled to still pot 2 (FIG. 1) for further use according to the method of the invention and thereby lowering waste from the system.

During operation of the second distillation apparatus for separation of the EDC from chloral, additional water is removed from the chloral as an overhead stream containing EDC, water, chloral and chloral hydrate. This stream may be returned to the azeotropic distillation previously described for further use according to the method of the invention.

In an alternative embodiment of the invention, the separation of the dehydrating agent from the chloral will be performed with the azeotropic distillation in a single column in a batchwise or continuous manner. An example of this embodiment is described with respect to FIG. 2.

Figure 2:
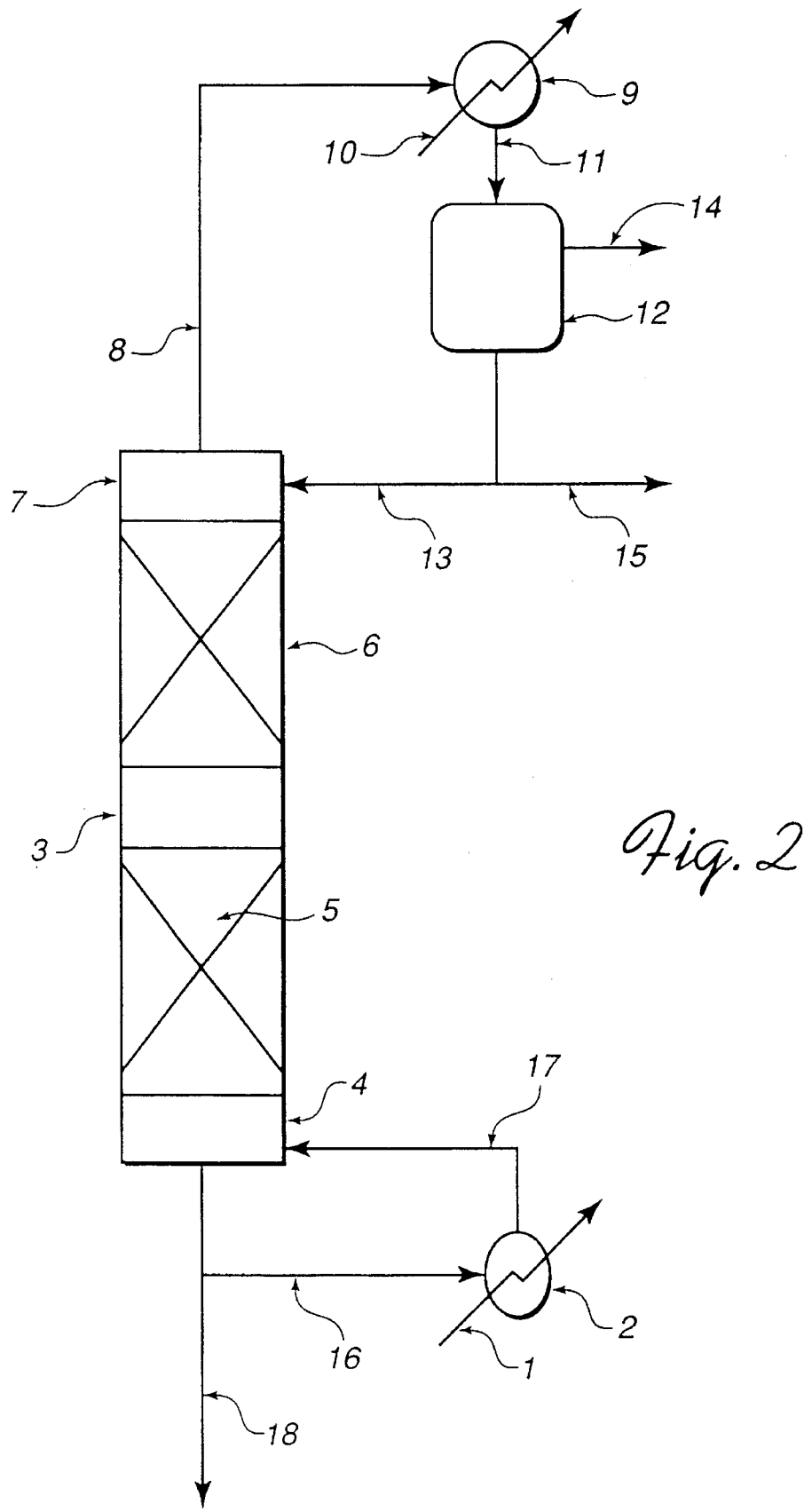
FIG. 2 schematically depicts an exemplary single column distillation apparatus for use in practicing the method of the invention. Flow of the charged stream through the apparatus and recovery of components therefrom are indicated by arrows at appropriate junctures in the Figure.

Referring now in detail to FIG. 2, there is shown a distillation apparatus to which the feed stream is fed through line 3. This stream will contain at least 60% chloral and less than 40% water. EDC may be added to, or contained in, this feed stream or be introduced into the column at a point above or below the chloral concentrate feed point (line 3). In distillation column 6 packed with packing material 5, the chloral composition is countercurrently contacted with reboiled vapors of EDC and chloral. Bottoms liquid is passed through line 16 to reboiler 2 heated by steam or other means introduced through line 1. In reboiler 2 the bottoms liquid is boiled producing the reboiled vapors which in turn return to the distillation column 6 at its bottom end 4 through line 17. A portion of the bottoms liquid, of which chloral is the principal constituent is drawn off through line 18 as a product. This chloral product composition contains less than 1000 parts of water per million parts relative to the chloral by weight.

Overhead or head product from the distillation of the feed stream is passed from the top of the column 7 through line 8 into condenser 9 cooled by coolant passing through line 10. In condenser 9, most of the by-product composition is condensed to a liquid, in either one or two phases. The material is passed to decanter 12 through line 11. After separation and removal of any aqueous phase via line 14, the EDC can be returned via line 13 for reflux through column 6, or alternatively can be drained from the system through line 15.

To further illustrate the method of the invention, examples are provided below of an azeotropic distillation of a feed stream and separation of chloral from the dehydrating agent. Although many of the examples illustrate the use of the method in the apparatus of FIG. 1, it will be understood that the method can also be practiced in the apparatus of FIG. 2. An illustration of how the method may be practiced in the apparatus of FIG. 2 is provided in Example III.

EXAMPLE I

"Chloral" as used in this and following examples should be understood to include both free chloral and chloral hydrate in aqueous solution.

As the distillation proceeds, the chloral containing feed stream is contacted in a countercurrent manner with the EDC. Still pot 2 serves as a reboiler in the process to produce reboiled vapors of the bottom product for reintroduction into column 6 until the all the water is removed (distillation is complete). The top product is condensed to liquid, water and EDC are separated and the EDC is returned continuously for reflux to the top of column 6.

Using the Karl Fischer method for measuring water content well-known to those skilled in the art and an acid base titration for determination of the chloral content, the percent by weight of each component in the various streams produced at various times during the distillation process was measured.

The effect of variations in the EDC to chloral ratio during the azeotropic drying step is demonstrated by the following tables of data generated from EDC distillation of chloral in the apparatus of FIG. 1. These data also demonstrate that recovery of anhydrous chloral is enhanced as the length in time of the distillation is increased.

Also, although the data is not shown, decreases in the inner diameter of the distillation columns as well as increases in the length of the distillation columns may also enhance the recovery of anhydrous chloral.

EXPERIMENT A

Charged Composition: 60.1% by wt chloral to 39.9% by wt water (904 grams to 600 grams). EDC added: 126 grams. Chloral/EDC ratio: 7.2:1

TABLE 1

| TIME (hr) | HEAD TEMPERATURE (°C.) | POT TEMPERATURE (°C.) | TOTAL AQUEOUS VOLUME COLLECTED (mL) |
|---|---|---|---|
| 1 hr | 72 | 93.0 | 50 mL |
| 1.75 hr | 72 | 97.0 | 135 mL |
| 2 hr | 72 | 95.0 | — |
| 2.25 hr | 72 | 98.5 | 215 mL |
| 3 hr | 72 | 97.0 | 295 mL |
| 3.25 hr | 73 | 97.0 | 340 mL |
| 3.5 hr | 74.5 | 98.5 | 410 mL |
| 4 hr | 75.0 | 97.0 | 470 mL |
| 4.5 hr | 75.0 | 97.0 | 510 mL |
| 6 hr | 85.0 | 100 | 620 mL |

Analysis Results

Total Chloral carried overhead in aqueous phase: 48.4 grams
Chloral contained in overhead EDC phase: 4.7 grams
Total Chloral carried overhead as a percent of charged: 5.4%
Final Still Pot Composition: (985 grams)
0.135% water, 82% chloral (EDC makes up balance)

EXPERIMENT B

Charged Composition: 59.1% by wt chloral to 40.9% by wt water (1205 grams to 800 grams). EDC added: 88 grams. Chloral/EDC ratio: 13.7:1

TABLE 2

| TIME (hr) | HEAD TEMPERATURE (°C.) | POT TEMPERATURE (°C.) | TOTAL AQUEOUS VOLUME COLLECTED (mL) |
|---|---|---|---|
| 0.5 hr | 72.0 | 96.5 | 60 mL |
| 0.75 hr | 72.0 | 98.5 | 90 mL |
| 1.25 hr | 72.0 | 99.0 | 185 mL |
| 2.75 hr | 73.5 | 102.0 | 460 mL |
| 3.5 hr | 75.5 | 100.0 | 590 mL |
| 4 hr | 76.0 | 100.0 | 680 mL |
| 4.75 hr | 77.5 | 98.5 | 765 mL |
| 5 hr | 80.0 | 99.0 | 790 mL |
| 5.25 hr | 79.0 | 99.0 | 815 mL |

Analysis Results

Total Chloral carried overhead in aqueous phase: 77.2 grams
Chloral contained in overhead EDC phase: 27.6 grams
Total Chloral carried overhead as a percent of charged: 8.7%
Final Still Pot Composition: (1134.2 grams)

0.93% water, 90.8% chloral (EDC makes up balance)

NOTE: This distillation was stopped because phase separation was limited. It is believed that the separation was impeded by the lack of distinction between the density of the overhead aqueous layer and the EDC layer.

EXPERIMENT C

Charged Composition: 59.1% by wt chloral to 40.9% by wt water (904 grams to 600 grams). EDC added: 630 grams. Chloral/EDC ratio: 1.4:1

TABLE 4

| TIME (hr) | HEAD TEMPERATURE (°C.) | POT TEMPERATURE (°C.) | TOTAL AQUEOUS VOLUME COLLECTED (mL) |
|---|---|---|---|
| 0.5 hr | 71.5 | 78.0 | 35 mL |
| 1.5 hr | 71.7 | 81.0 | 240 mL |
| 2 hr | 71.9 | 83.0 | 350 mL |
| 2.5 hr | 72.8 | 85.0 | 425 mL |
| 2.75 hr | 73.0 | 85.0 | 440 mL |
| 3.25 hr | 74.5 | 88.0 | 520 mL |
| 3.5 hr | 75.5 | 89.5 | 560 mL |
| 3.75 hr | 80.0 | 93.0 | 590 mL |
| 4 hr | 82.5 | 93.5 | 595 mL |
| 4.5 hr | 83.2 | 94.0 | 600 mL |
| 5 hr | 83.5 | 94.0 | 614 mL |
| 5.5 hr | 83.5 | 94.0 | — |

Analysis Results

Total Chloral carried overhead in aqueous phase: 9.8 grams
Chloral contained in overhead EDC phase: 5.6 grams
Total Chloral carried overhead as a percent of charged: 1.1%
Final Still Pot Composition: (1501.7 grams)
270 ppm water, 58.7% chloral (EDC makes up balance)

EXPERIMENT D

Charged Composition: 59.1% by wt chloral to 40.9% by wt water (904 grams to 600 grams). EDC added: 315 grams. Chloral/EDC ratio: 2.9:1

TABLE 5

| TIME (hr) | HEAD TEMPERATURE (°C.) | POT TEMPERATURE (°C.) | TOTAL AQUEOUS VOLUME COLLECTED (mL) |
|---|---|---|---|
| 0.5 hr | 72.0 | 84.0 | 35 mL |
| 1 hr | 72.0 | 84.0 | 140 mL |
| 1.75 hr | 72.0 | 89.0 | 280 mL |
| 2.25 hr | 74.0 | 90.0 | 410 mL |
| 2.75 hr | 74.5 | 91.0 | 490 mL |
| 3 hr | 76.0 | 92.0 | 530 mL |
| 3.25 hr | 78.0 | 94.0 | 570 mL |
| 3.75 hr | 82.0 | 96.0 | 600 mL |
| 4 hr | 83.5 | 97.5 | 605 mL |
| 4.5 hr | 83.5 | 98.0 | — |
| 5 hr | 83.5 | 99.0 | — |

Analysis Results

Total Chloral carried overhead in aqueous phase: 19.5 grams
Chloral contained in overhead EDC phase: 4.9 grams
Total Chloral carried overhead as a percent of charged: 2.2%
Final Still Pot Composition: (1168.2 grams)
425 ppm water, 69.3% chloral (EDC makes up balance)

EXPERIMENT E

Charged composition: same as in Example I-D
EDC added: same as in Example I-D
Chloral/EDC ratio: same as in Example I-D

TABLE 6

| TIME (hr) | HEAD TEMPERATURE (°C.) | POT TEMPERATURE (°C.) | TOTAL AQUEOUS VOLUME COLLECTED (mL) |
|---|---|---|---|
| 0.5 hr | 72.0 | 86.0 | 45 mL |
| 0.75 hr | 72.0 | 87.0 | 90 mL |
| 1.75 hr | 72.0 | 92.0 | 315 mL |
| 2.25 hr | 73.5 | 92.5 | 420 mL |
| 2.75 hr | 74.0 | 94.0 | 495 mL |
| 3.25 hr | 78.5 | 97.0 | 590 mL |
| 3.75 hr | 82.5 | 99.0 | 600 mL |
| 4.5 hr | 83.2 | 99.0 | 605 mL |
| 5.25 hr | 83.2 | 99.0 | — |
| 5.5 hr | 83.2 | 99.0 | — |

Analysis Results

Total Chloral carried overhead in aqueous phase: 3.2 grams
Chloral contained in overhead EDC phase: 0.5 grams
Total Chloral carried overhead as a percent of charged: 0.35%
Final Still Pot Composition: (1186.5 grams)
235 ppm water, 71.5% chloral (EDC makes up balance)

EXPERIMENT F

Charged composition: same as in Example I-D
EDC added: same as in Example I-D
Chloral/EDC ratio: same as in Example I-D

TABLE 7

| TIME (hr) | HEAD TEMPERATURE (°C.) | POT TEMPERATURE (°C.) | TOTAL AQUEOUS VOLUME COLLECTED (mL) |
|---|---|---|---|
| 1 hr | 71.8 | 88.0 | 140 mL |
| 2 hr | 71.8 | 90.5 | 280 mL |
| 2.5 hr | 72.7 | 94.0 | 400 mL |
| 3 hr | 74.0 | 94.0 | 470 mL |
| 3.5 hr | 74.0 | 95.0 | 530 mL |
| 4.5 hr | 78.0 | 97.0 | 570 mL |
| 4.75 hr | 82.0 | 97.0 | 580 mL |
| 5 hr | 83.0 | 98.0 | 590 mL |
| 6 hr | 83.1 | 100.0 | 600 mL |
| 6.5 hr | 83.1 | 100.0 | 606 mL |

Analysis Results

Total Chloral carried overhead in aqueous phase: 3.62 grams
Chloral contained in overhead EDC phase: 0.53 grams
Total Chloral carried overhead as a percent of charged: 0.40%
Final Still Pot Composition: (1182.0 grams)
150 ppm water, 75.4% chloral (EDC makes up balance)

EXAMPLE II

This example is a continuation of the process shown in Example I wherein the dried Chloral/EDC product composition is subjected to continued distillation for separation of the chloral from the EDC.

To this end a combined total of 1804.9 grams of feed stream and EDC are charged to still pot 2 and brought to a temperature of 95° C. The overhead temperature at this point is 80° C. The composition of the feed stream charged is 3000 PPM $H_2O$, 78.3% by weight chloral (1287 grams) and 28.4% by weight EDC (512.6 grams). The apparatus was operated as a rectification apparatus and the reflux ratio was set as 21:1, reflux returned to the column through line 13 versus that drawn out of the system through line 15.

TABLE 8

| TIME (HRS) | HEAD TEMP (°C.) | POT TEMP (°C.) | FRACT.# /VOLUME (mL) | WEIGHT (GRAMS) | % CHLORAL | GRAMS CHLORAL | GRAMS EDC |
|---|---|---|---|---|---|---|---|
| 0   | 80.0 | 95.0  | 0     | 0    |        |      |      |
| 1   | 79.8 | 95.2  | 0     | 0    |        |      |      |
| 2   | 81.7 | 95.8  | 1.48  | 59.2 |        |      |      |
| 2.5 | 82.0 | 96.5  | 2.39  | 47.8 |        |      |      |
| 3   | 82.5 | 97.0  | 3.55  | 68.7 |        |      |      |
| 3.5 | 82.6 | 97.5  | 4.52  | 63.9 |        |      |      |
| 4   | 82.9 | 98.0  | 5.49  | 60.0 |        |      |      |
| 4.5 | 83.3 | 99.0  | 6.51  | 62.6 | 4.1%   | 2.6  | 60.0 |
| 5   | 83.8 | 99.9  | 7.54  | 67.1 | 7.24%  | 4.9  | 62.2 |
| 5.5 | 84.7 | 101.0 | 8.45  | 56.3 | 14.97% | 8.4  | 47.9 |
| 6   | 86.7 | 102.0 | 9.53  | 71.7 | 45.7%  | 32.8 | 38.9 |
| 6.5 | 93.5 | 102.5 | 10.56 | 81.0 | 84.82% | 68.7 | 12.3 |
| 7   | 97.4 | 103.5 |       |      |        |      |      |

Analysis Results

Total Chloral carried overhead: 141.8 grams
Total Chloral carried overhead as a percent of charged: 11.0%
Final Still Pot Composition: (1146.3 grams)
87 ppm water, 99.8% chloral, 0.2% EDC.

EXAMPLE III

As an example of the method of the invention which can be done on a continuous basis, refer to the apparatus and flow sheet illustrated in FIG. 2. The distillation apparatus is fed through line 3, a stream which contains 60% chloral, 35% water and 15% EDC. In distillation column 6 packed with packing material 5, the chloral composition is countercurrently contacted with reboiled vapors of EDC and chloral. Bottoms liquid passing through line 16 to reboiler 2 is heated to boiling, producing the reboiled vapors which in turn are returned to the distillation column. A portion of the bottoms liquid (chloral) is drawn off through line 18 as a product composition. This chloral product composition contains less than 1000 parts of water per million parts relative to the chloral by weight.

Vapors from the distillation passed from the top of the column are condensed to a liquid, either one or two phases, in condenser 9. The material is passed to decanter 12 through line 11. After separation of any phases present in the decanter, the aqueous phase is removed via line 14, the EDC is returned to the column as reflux and is continuously drained from the system through line 15.

We claim:

1. A process of azeotropic distillation of chloral comprising:

charging a feed stream including at least 60% by weight chloral and containing less than 40% by weight water and wherein the feed stream contains at least some ethylene dichloride to a distillation column having at least 6 theoretical trays therein;

adding additional ethylene dichloride when needed to the distillation column to that the ratio of the concentration of chloral in the feed stream to that of the ethylene dichloride is less than about 14:1 at the time the feed stream is charged to the distillation column to form an azeotropic mixture in the distillation column;

bringing the azeotropic mixture to a boil at a pressure consisting of atmospheric pressure;

allowing the distillation to proceed to completion;

recovering an anhydrous chloral product containing less than 0.1% by weight water; and separating the ethylene dichloride from the recovered anhydrous chloral product by further distillation thereof.

2. A process according to claim 1 wherein said feed stream further is an aqueous stream resulting from the manufacture of ethylene dichloride.

3. A process according to claim 1 wherein said feed stream further is an aqueous stream resulting from the manufacture of vinyl chloride.

4. A process according to claim 1 wherein said feed stream further is an aqueous stream isolated from the oxychlorination of ethylene.

5. A process according to claim 1 wherein said feed stream is charged to a distillation column having at least 12 theoretical trays.

6. A process according to claim 1 wherein said feed stream is charged to a distillation column having between 24 and 26 theoretical trays.

7. A process according to claim 1 wherein said theoretical trays are formed in packing contained in the distillation column.

8. A process according to claim 1 wherein the ratio of the concentration of chloral to ethylene dichloride in the azeotropic mixture is between about 1.4:1 and 14:1.

9. A process according to claim 1 wherein the further distillation step occurs in the distillation column used for the azeotropic distillation step.

10. A process according to claim 1 wherein the further distillation step occurs in a distillation column separate from the column used for the azeotropic distillation step.

* * * * *